United States Patent [19]

Seipke et al.

[11] Patent Number: 4,526,717

[45] Date of Patent: Jul. 2, 1985

[54] POLYPEPTIDE HAVING AN ACTION ON THE IMMUNOLOGICAL SYSTEM, PROCESSES FOR ITS ISOLATION AND PURIFICATION, ITS USE, AGENTS CONTAINING THIS COMPOUND, AND ITS CLEAVAGE PRODUCTS, THEIR USE AND AGENTS CONTAINING THESE PRODUCTS

[75] Inventors: Gerhard Seipke, Wiesbaden; Dominique Tripier, Eppstein; Gerd Johnscher, Kelkheim, all of Fed. Rep. of Germany

[73] Assignee: Hoechst Aktiengesellschaft, Frankfurt am Main, Fed. Rep. of Germany

[21] Appl. No.: 627,647

[22] Filed: Jul. 3, 1984

Related U.S. Application Data

[62] Division of Ser. No. 522,204, Aug. 11, 1983, Pat. No. 4,500,450.

[30] Foreign Application Priority Data

Aug. 13, 1982 [DE] Fed. Rep. of Germany ....... 3230151

[51] Int. Cl.³ .................... C07C 103/52; C07G 7/00
[52] U.S. Cl. .................... 260/112.5 R; 260/112 R; 260/112.5 TR; 514/12
[58] Field of Search .................... 260/112 R, 112.5 R, 260/112.5 T, 112.5 TR; 424/177

[56] References Cited

U.S. PATENT DOCUMENTS

| | | | |
|---|---|---|---|
| 4,010,148 | 3/1977 | Goldstein | 260/112 R |
| 4,055,633 | 10/1977 | Goldstein | 436/539 |
| 4,077,949 | 3/1978 | Goldstein | 260/112.5 R |
| 4,079,127 | 3/1978 | Goldstein et al. | 260/112.5 R |
| 4,120,951 | 10/1978 | Goldstein | 424/177 |
| 4,261,886 | 4/1981 | Goldstein | 260/112.5 R |
| 4,389,343 | 6/1983 | Horecker | 260/112.5 R |
| 4,395,404 | 7/1983 | Low et al. | 424/177 |

Primary Examiner—John Kight
Assistant Examiner—Nathan M. Nutter
Attorney, Agent, or Firm—Finnegan, Henderson, Farabow, Garrett & Dunner

[57] ABSTRACT

The invention relates to a polypeptide which can be isolated from thymus glands and has an action on the immunological system, and which has a molecular weight of 3,480, a UV absorption with a maximum at 205 to 210 nm and an isoelectric point of 3.95+0.15 and a specific aminoacid composition, the N-terminal, if appropriate, carrying an acyl group or an acylglycyl group, processes for its isolation and purification, its use, agents containing this polypeptide, and its cleavage products, their use and agents containing them.

3 Claims, 5 Drawing Figures

POLYPEPTIDE HAVING AN ACTION ON THE IMMUNOLOGICAL SYSTEM, PROCESSES FOR ITS ISOLATION AND PURIFICATION, ITS USE, AGENTS CONTAINING THIS COMPOUND, AND ITS CLEAVAGE PRODUCTS, THEIR USE AND AGENTS CONTAINING THESE PRODUCTS

This is a division of application Ser. No. 522,204, filed Aug. 11, 1983, now U.S. Pat. No. 4,500,450.

The invention relates to a hitherto unknown polypeptide which can be isolated from thymus glands and has an action on the immunological system, and which has a molecular weight of 3,480, a UV absorption with a maximum at 205 to 210 nm, an isoelectric point of 3.95±0.15 and the following aminoacid composition: 4 asparaginic acid units, 3 threonine units, 3 serine units, 6 glutamic acid units, 1 glycine unit, 4 alanine units, 3 valine units, 1 isoleucine unit, 1 leucine unit, 5 lysine units and 1 arginine unit, the N-terminal, if appropriate, carrying an acyl group having 1 to 6 atoms or an acylglycyl group, the acyl group of which has 1 to 6 carbon atoms, and to its peptide cleavage products and pharmacologically acceptable salts.

It is known that cell-free protein extracts from thymus glands of calves (for example thymosin fraction 5, which is a known standard product) can be used to suppress immunological deficiency symptoms which, for example, can cause reduced graft rejection, increased probability of oncogenesis, increased susceptibility to infection, and accelerated aging processes. The successful clinical use of this fraction 5, in particular on lung cancer patients, has been reported (P. B. Chretien et al. Cancer Treat. Rep. 62 (1978) 1787–1790).

For obvious reasons, it is desirable in a therapy, instead of a mixture of substances which possibly also contains inhibitors of the desired effect or even toxic compounds, to use characterized pure substances having a defined and reproducible activity. Furthermore, the composition of such a mixture of substances is difficult to standardize, since the composition depends, inter alia, on the age of the animals slaughtered. Examples of such pure substances which have been isolated from mixtures are thymosin $\alpha_1$, $\beta_1$, $\beta_4$, $\beta_8$ and $\beta_9$, the first of the substances mentioned having been the most thoroughly investigated with regard to its biological action (T. L. K. Low et al. J. Biol. Chem. 254 (1979) 981–986, T. L. K. Low et al. Proc. Natl. Acad. Sci. USA 78 (1981) 1162–1166).

Very recently, however, reports have appeared in particular on thymosin $\alpha_1$ and $\beta_8$ (E. Hannappel et al. Proc. Natl. Acad. Sci. USA 79 (1982) 1708–1711), and the present work on the isolation of the peptide according to the invention supports these findings that both peptides result only as a consequence of an isolation technique which is not mild and therefore difficult to reproduce (thymosin $\alpha_1$ could not be detected in secondary fractions in the isolation of the hormone according to the invention).

It was therefore the object of the invention to isolate pure hormones under mild conditions in order thereby to retain the intact natural active principles. Since there is a large number of such active principles in the thymus gland, and this plurality is certainly of significance, for example with regard to varying specificity of action, the purification of all these substances is of the greatest importance for providing an optimum spectrum for the therapy of the abovementioned disorders.

The peptide isolated according to the invention has a high purity, preferably above 90%, as can be readily shown using methods conventionally employed in peptide chemistry. These methods include polyacrylamide gel electrophoresis, isoelectric focusing and aminoacid analysis. The novel compound can be obtained in equally good yield and in the same high purity in different variants of the working up procedure according to the invention, the products of all working up processes being identical to one another. This indicates that it is an intact natural substance and not a cleavage product dependent on the working up procedure.

The peptide according to the invention is white, odorless and stable in neutral solution at elevated temperature, for example 80° C., and can be stored in the dry form at temperature below +5° C. for at least 3 years without loss in activity. From its chemical structure, it is a polypeptide in which, after complete hydrolytic cleavage, no other constituents can be detected apart from the aminoacids.

If the aminoacid composition is determined by the method of Moore and Stein (Methods of Enzymology Volume VI, 819–831, published by Colovick and Kaplan, Academic Press, New York, London, 1963), the following values are found: 4 asparaginic acid units, 3 threonine units, 3 serine units, 6 glutamic acid units, 1 glycine unit, 4 alanine units, 3 valine units, 1 isoleucine unit, 1 leucine unit, 5 lysine units and 1 arginine unit.

A characterizing feature of the polypeptide according to the invention is the absence of methionine, cysteine, histidine, phenylalanine, tyrosine and tryptophan. The absence of, in particular, methionine and the aromatic aminoacids can be used in the concentration processes for evaluating the purity of the fractions. It also provides the additional explanation for the fact that no exact correlation exists between the peak areas in the chromatographic separation and the amount of substance isolated from the peak when detection is effected at the conventionally used wavelength of 254 nm. SDS-polyacrylamide gel electrophoresis (J. O. Thomas in: Techniques in Protein and Enzyme Biochemistry B 106, 102 et seq. (1978) Elsevier/North Holland, Biomedical Press) is used for the molecular weight determination, a value of about 3,000–4,000 being obtained when the migration zone of the polypeptide is compared with that of known reference substances, such as, for example, trypsin inhibitor from soyabean (molecular weight 6,000) and insulin B-chain (molecular weight 2,500). This result correlates with the findings of the aminoacid analysis.

In basic disc electrophoresis in polyacrylamide gel (L. Ornstein, Ann. N.Y. Acad. Sci. 121 (1964) 321–349 and B. J. Davies, Ann. N.Y. Acad. Sci. 121 (1964) 404–427), the product according to the invention essentially shows a single band with a Rf value of 0.5 to 0.6. Isoelectric focusing in 0.3 mm thick gels which have been prepared by the technique of Radola (B. J. Radola, Elektrophoresis 1 (1980) 43–46) and contain ampholytes for the pH range 2–9 and 6M urea shows a similar pattern. The isoelectric point of the polypeptide according to the invention, i.e. 3.95±0.15, is ascertained by comparison with commercially obtainable test mixtures; the error range given results from the fact that the samples and comparison never have exactly the same ionic strength, and even the urea necessary for obtaining high resolution can influence the isoelectric point of polypeptides. Such polyacrylamide gels are stained with a modified Coomassie blue (Blakesley and Boezi, Analytical Biochemistry 82 (1977) 580–582).

The invention furthermore relates to a process for isolating this purified polypeptide, which comprises isolating the polypeptide from the thymus with the aid of a combination of precipitation methods, membrane filtrations and chromatography.

The thymus glands are preferably extracted with an aqueous solution of an inorganic salt having a buffering action in the pH range from 5.0 to 9.0, preferably phosphate. The insoluble material is removed and the polypeptide is separated off from the resulting extract and isolated.

The chromatography step of the above isolation process preferably comprises cation and/or anion exchange chromatography, chromatography on non-specific adsorbants, in particular hydroxyapatite, partion chromatography, in particular partition between two immiscible media, one of which contains a large amount of water, or a combination of two or more of these methods.

It is advantageous to use for this chromatography an extract which has been subjected to heat-denaturing, the peptide according to the invention remaining in solution and retaining its complete activity whilst other proteins can be separated off by sedimentation or filtration. A material which is separated off as a precipitate on treatment of the extract by addition of water-miscible organic solvents, preferably acetone, can also be used for the chromatography. Similarly, it is possible to use an extract which has been subjected to fractional precipitation by addition of water-soluble inorganic and/or organic salts, preferably ammonium sulfate, the peptide precipitating in certain concentration ranges, which depend on the salt used, and being concentrated by sedimentation techniques. An extract which, as a result of fractionation by means of membrane filtration and/or gel filtration, still contains only peptides having a molecular weight below 10,000 Daltons can furthermore be used for the chromatography.

Extracts which have been obtained by a combination of two or more of the processes described above could of course also be used for the chromatography.

The starting material for the preparation of the polypeptide according to the invention consists of fresh thymus glands or such gland material which has been stored in a deep-frozen state promptly after slaughter. An aqueous extract is prepared from this material by comminution in the frozen state and addition of a salt solution, with further cooling (0° to +4° C.). It is advantageous to subject this extract to an optimum temperature of between 70° to 90° C., preferably 80° C., by rapid heating, because most of the proteases are thereby inactivated and separated off as a precipitate. Separation is effected by centrifugation and filtration over gauze.

Comparison with other protease inactivation methods, such as the addition of chemical inactivators, for example phenylmethylsulfonyl fluoride (PMSF) has shown that neither the yield nor the activity drops solely by heat treatment, and that this process is thus adequate per se for this purpose.

In order to obtain smaller volumes and hence to facilitate further working up, the protein fraction of interest should be concentrated out of the heat-treated extract by precipitation. This precipitation can be carried out by adding the extract to a water-miscible organic solvent. For example, several times the extract volume, preferably 5 times the amount, of acetone can be used, the precipitation being carried out at very low temperatures of between −10° and −30° C., preferably at −20° C. It is also important to filter or centrifuge the mixture as rapidly as possible, since other concomitant substances are also precipitated if the mixture is left to stand for a prolonged period. In this step also, enzymes possibly remaining in solution are inhibited by the high concentration of organic solvent. The precipitate thus obtained can be stored in the frozen state without loss of activity.

Another possibility of concentration by precipitation, which can be carried out either instead of or after the abovementioned method, is the addition of neutral salts, such as, for example, ammonium sulfate. The precipitation can achieve a certain selectivity by pH control. By addition of ammonium sulfate to 50% saturation, the peptide according to the invention, which has an isoelectric point of about 3.95, can be precipitated in the pH range between 3 and 5, preferably at pH 4, such that a large number of concomitant proteins remain in solution. This precipitation is also carried out with cooling, preferably at between 0° and +4° C.

Two methods have proved suitable for separating off other proteins having a similar isoelectric point but a higher molecular weight: gel filtration and ultrafiltration, the latter being particular suitable on an industrial scale. Gel filtration permits division into narrower molecular weight ranges, but is of more limited capacity than ultrafiltration, so that it seems more suitable for later steps in the course of working up relatively large amounts of extract, for example subsequent purification of ultrafiltration or column chromatography fractions. Spherical particles based on crosslinked dextran, polyacrylamide or modified silica gel, for example BioGel ®, Sephadex ®, Ultrogel ® or a polyol having a fractionation range of up to 10,000 Daltons, are best used for the gel filtration. Because of the isoelectric point of the product according to the invention, the gel filtration, as is in fact the case with all further purification steps, is best carried out in aqueous buffers at pH values between 4 and 9, since otherwise the solubility of the polypeptide is not ensured.

With two exceptions (CM-cellulose and hydroxyapatite, see below), the pH range of 7.5–8.5 (ammonium bicarbonate or tris/HCl) has proved to be particular advantageous.

The ultrafiltration is best carried out in two stages so that the membranes are not too heavily loaded (blockage of the pores). It has proved advantageous, for example, to use a capillary membrane having an exclusion limit of 50,000 Daltons in combination with a flat membrane having an exclusion limit of 10,000 Daltons. Rapid removal of higher-molecular material which would reduce the flow through the more selectively operating flat membrane is achieved with the capillary membrane.

On the basis of the method hitherto used, the material thus obtained still consists of a mixture of polypeptides. Because of its isoelectric point, the polypeptide according to the invention does not bond to a cation exchanger at the conventionally used pH range of 4 to 5, so that, with the aid of these exchangers based on cellulose, dextran, polyacrylamide, polystyrene resin or silica gel, it can rapidly be separated off from a large amount of the concomitant products which have an isoelectric point above pH 4 to 5 and are therefore absorbed. This separation can be effected in a chromatography column or in a batch process.

Figure 2:
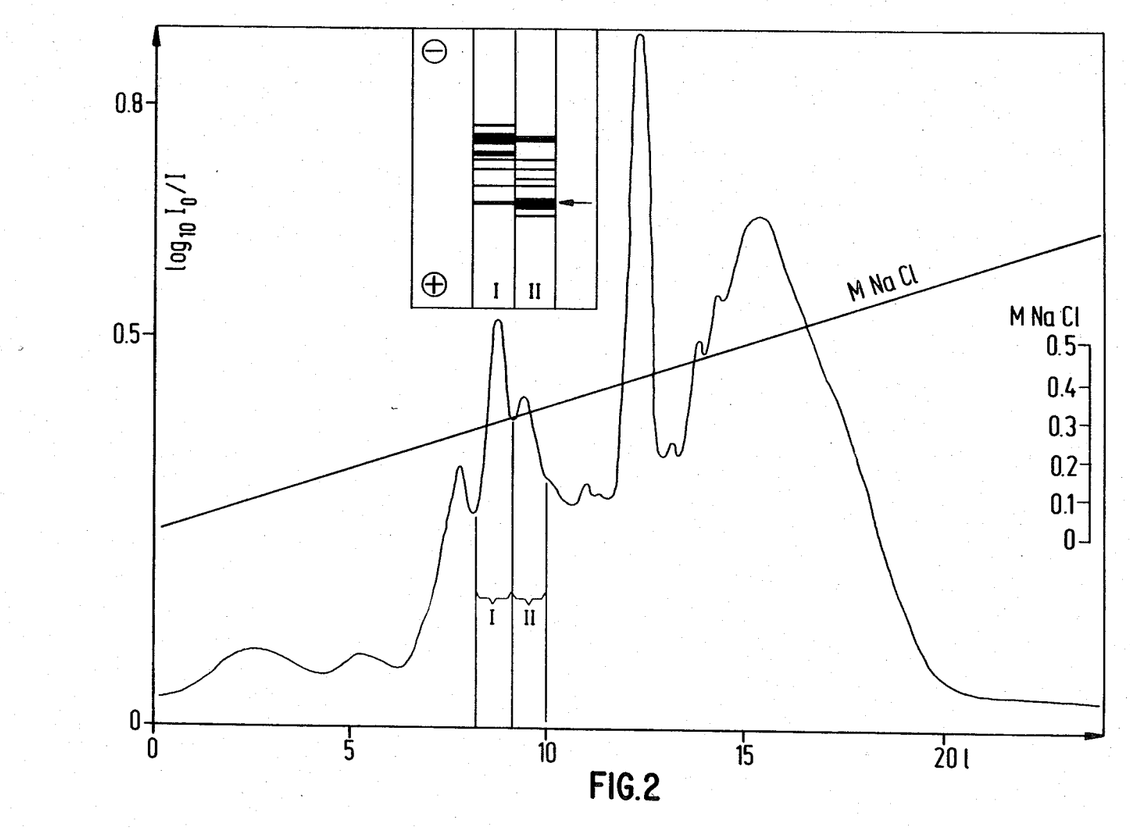

In contrast, the peptide is bonded to an anion exchanger based on dextran, polyacrylamide, cellulose, polystyrene resin or silica gel at pH values of 5 to 9, preferably 8, and can be eluted substantially selectively by choosing suitable conditions. Examples of such conditions are application of a pH or salt gradient. It has proved advantageous to use a 50 millimolar tris-HCl buffer, pH 8, and a sodium chloride gradient of 0 to 0.5M distributed over 5 to 10 times the column volume. Before this chromatographic separation, the polypeptide mixture shows a large number of bands, which can scarcely be resolved, in basic gel electrophoresis; staining with Coomassie blue gives the impression of a continuous background color with only very few defined bands. At this stage, the polypeptide according to the invention is not visible. A clear picture is obtained only on analysis of the ion exchanger fraction. Almost every peak of the chromatography can be correlated with a definite band of the electrophoresis, so that localization of the peptide according to the invention is possible at about 35% of the gradient described in Example 7 (cf. FIG. 2).

Because of the complexity of the chromatogram, achievement of complete homogeneity in this first chromatography step is not ensured. A good further purification effect can be achieved by rechromatography over the same separation system. Gel filtration also separates off a further small amount of higher-molecular material. However, the degree of purity is only slightly increased in this case, since the material has already passed intensively through this separation principle (ultrafiltration).

Figure 3:
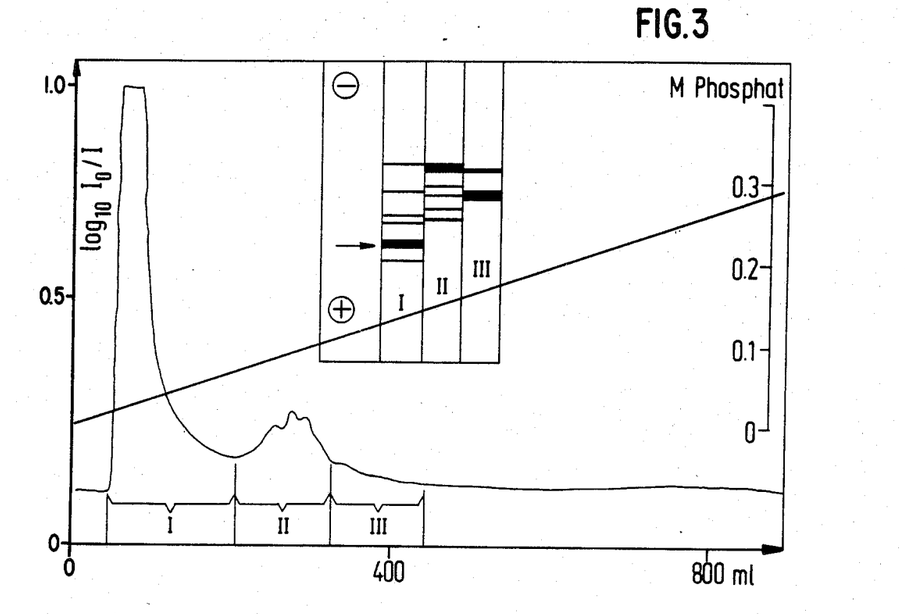

It is advantageous to use a completely different method, i.e. absorption on hydroxyapatite, before or after the rechromatography on ion exchangers, since this process is carried out with small losses and rapidly because the polypeptide according to the invention flows through the separating column unretarded in the conventionally used 10 millimolar phosphate buffer at pH 6.8, and only concomitant substances are bonded (cf. FIG. 3).

Figure 5:
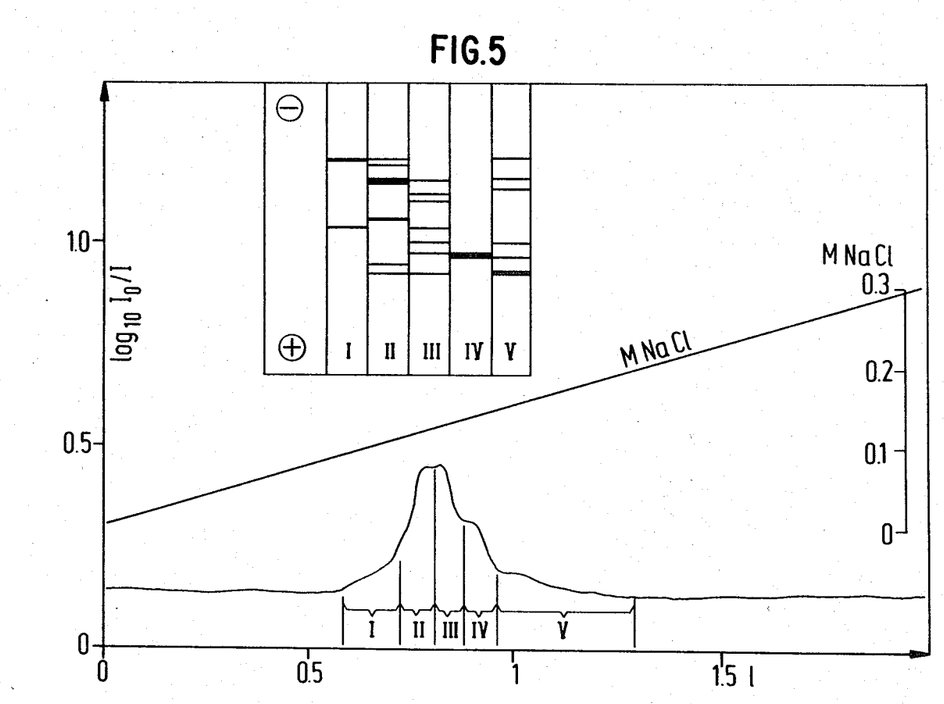

Chromatography on hydroxyapatite is generally included before the final purification by rechromatography on an anion exchanger, but this method can also be used with equal success at another point in the working up scheme (for example after the cation exchanger). The rechromatography step on an anion exchanger is carried out in a column of low volume and having a substantially flatter gradient course (cf. FIG. 5).

It is self-evident that demineralization and lyophilization follow each purification step. Only the material obtained from the cation exchanger treatment can, since its salt content is low, be used directly for the next step. The salts are removed either by ultrafiltration over a suitable flat membrane having an exclusion limit of 500 Daltons or 10,000 Daltons, or by gel filtration over a suitable material based on crosslinked dextran or polyacrylamide, for example Sephadex G 10 or G 25, Bio Gel P-2 or Ultrogel ACa 202.

Buffers which can be removed during subsequent lyophilization, for example ammonium bicarbonate, are of course best used.

The polypeptide according to the invention, the N-terminal of which is present as the free base, can be converted into the corresponding N-acyl or N-acylglycyl derivative in a manner which is known per se, acyl preferably being Boc or $C_1$-$C_6$-alkanoyl, in particular acetyl.

Pharmacologically acceptable salts of the peptide according to the invention are understood as meaning, in particular, alkali metal and alkaline earth metal salts, but also physiologically acceptable salts with amines, such as alkylamines and cycloalkylamines.

The peptide according to the invention has been found to be active in various conventional in vitro tests in respect of an action which influences the immunological system. These include T cell differentiation, the extent of which is measured by the E-rosette test (Aiuti, Scand. J. Immunol., 3, 521–532, 1974) and the phytohemaglutinin stimulation test (PHA stimulation test).

In the spontaneous rosette test, the naturation of lymphocytes from human umbilical cord blood is effected by rosetting with sheep erythrocytes in the cold. Since only mature T cells form rosettes in the cold with sheep erythrocytes, this is a specific T cell test, i.e. it enables observation of the shift of T cells (so-called null cells, a relatively large number of which occur in umbilical cord blood) to $R^+$-T cells, i.e. mature T cells.

Because of the larger number of null cells, the normal value of rosette-forming cells from umbilical cord blood is lower than in the peripheral blood of adults. A low rosette number can be correlated with a low immune on the basis of investigations of the blood of patients suffering from autoimmune diseases or tumors. In the PHA stimulation test (PHA=phytohemaglutinin) or the lymphocyte transformation test, conclusions about the number of mature lymphocytes, i.e. lymphocytes which can be stimulated, are obtained, not by investigation of the surface structures, as in the spontaneous rosette test, but by the function test for ability to be stimulated with the plant lectin HA, which bonds particularly to mature T cells.

The T lymphocytes are stimulated to blastogenesis by lectin in a way similar to that caused by antibacterial or viral antigens. This leads to proliferation, either directly or by the secretion of lymphokines. The incorporation of radioactive thymidine within a certain time is then a measure of the number of stimulated cells. Since only the mature or immunologically potent lymphocytes are stimulated, the naturation, after incubation with the substance, of lymphocytes worked up from umbilical cord blood can be monitored by this test.

The peptide has also been recognised as particularly effective in respect of an increase in the level of T lymphocytes in experiments with lymphocytes from immuno-deficient patients, for example with Di George syndrome. The desired more powerful effect, which manifests itself in a substantially slower effective concentration, of the pure substance in comparison with the mixture corresponding to "fraction 5" could also be clearly seen here (cf. Table 1).

TABLE 1

| | "Fraction 5" | | | Hormone according to the invention | | |
|---|---|---|---|---|---|---|
| Dose µg/ml | 125 | 250 | 500 | 5 | 10 | 100 |
| Activity* | 311 | 244 | 111 | 133 | 322 | 88 |

*Concentration of T lymphocytes in % in comparison with the standard following incubation with fraction 5 or with the polypeptide according to the invention.

Surprisingly, the full level of immunological activity is also retained on fragmentation of the intact natural product by a chemical route or, preferably, with certain specific proteases, such as those having tryptic or chrymotryptic activity. Those peptidic cleavage products of the peptide according to the invention which contain 4 or more aminoacids are preferred.

Fragment mixtures from digestion with TPCK trypsin or TLCK chymotrypsin have been investigated intensively. The procedures with these two enzymes are reproducible to the extent that, according to electrophoresis, mixtures of the same composition are always formed.

The invention relates to the use of the peptide according to the invention, its derivatives and/or its cleavage products produced by a chemical or enzymatic route, for regulating or stimulating the immunological system, as a therapeutic or prophylactic agent.

The invention furthermore relates to medicaments having an immunostimulating or immunoregulating action which can be used for the treatment and prophylaxis of virus infections, immunodeficiency diseases oncogenesis (in particular carcinoses) and forms of accelerated aging processes and contain the polypeptide according to the invention and/or its N-acyl derivatives and/or at least one of its fragments in the free form or in the form of pharmacologically acceptable salts. In the therapy of malignant tumors, the peptides according to the invention can also be used in combination with cytostatic agents (cf., for example, Mutschler, Arzneimittelwirkungen [Drug Actions], Wissenschaftliche Verlagsgesellschaft mbH, Stuttgart, 1981, pages 599–608) and/or radiation measures.

The polypeptides according to the invention can be used parenterally (for example subcutaneously or intravenously) or via mucous membranes (for example nasally or enterally).

The dosage for parenteral administration is 0.01–50 mg/m$^2$ of body surface/day, depending on the type of disease. In serious cases, it can also be increased, since no toxic properties have yet been observed. In particularly serious cases, several administrations per week over a period of several weeks are recommended. As a result of the particular absorption properties, doses for nasal administration must be correspondingly higher.

For subcutaneous, intravenous or nasal administration, the compounds according to the invention or physiologically acceptable salts thereof are converted into a solution, suspension or emulsion, if desired with the conventional substances for this conversion, such as solubilizing agents, emulsifiers or other auxiliaries. Examples of possible solvents for the novel active compounds and the corresponding physiologically acceptable salts are: water, physiological saline solutions or alcohols, for example ethanol, propanediol or glycerol, as well as sugar solutions, such as glucose or mannitol solutions, or a mixture of the various solvents mentioned.

Parenteral administration can also be effected, for example, with external or implanted metering devices, such as, for example, automatic pumps, or in the form of a continuous drip.

In this case, it is advantageous for additives which stabilize against denaturation, such as are known, for example, from EP-A No. 18,609, to be added.

The compounds according to the invention can also be administered in the form of a medicament with a depot action. In the case of injection solutions, such a depot action can be achieved, for example, by dissolving or suspending the medicament in an oily vehicle, adding macromolecules which increase the viscosity and which delay the diffusion of the dissolved medicaments, absorbing the medicament onto suitable carrier molecules, for example aluminum hydroxide, or using crystal suspensions.

For an oral use form, the active compounds are mixed with the conventional additives for this, such as excipients, stabilizers or inert diluents, and are converted into a suitable administration form, such as tablets, dragees, push-fit capsules, alcoholic or oily suspensions or aqueous, alcoholic or oily solutions, by conventional methods. Examples of inert excipients which can be used are gum arabic, magnesium carbonate, potassium phosphate, lactose, glucose or starch, in particular corn starch. Formulation can be effected as either dry granules or moist granules. Examples of possible oily excipients or solvents are vegetable and animal oils, such as sunflower oil or cod liver oil.

An aqueous sterile solution of the polypeptide according to the invention, its derivatives and/or at least one of its fragments can contain agents for rendering the solution isotonic, such as, for example, about 0.9% strength sodium chloride or 1.7% strength glycerol, and, if appropriate, also preservatives, such as hydroxybenzoic acid or phenol.

EXAMPLE 1

500 g of frozen thymus glands are homogenized with 1.5 liters of ice-cold 0.09% strength sodium chloride solution and 5 ml of octanol in a mixer in the course of 3 minutes. After centrifugation at 0° C. and 10,000 rpm for 30 minutes, the still cloudy supernatant liquor is clarified further by means of filtration over 2 layers of gauze, and is then heated to 80° C. in the course of 15 minutes, while stirring. The resulting precipitate is separated off by filtration over 4 layers of gauze. The filtrate is rapidly cooled down to +4° C. by stirring in an ice-bath, and is run into 7.5 liters of acetone pre-cooled to −20° C. Another precipitate is formed, and is filtered off on a glass suction filter after 5 minutes and rinsed with 1 liter of cold acetone (−20° C.). After drying in vacuo, 6.1 g of a slightly yellowish powder with a protein content (determined by the Lowry method) of 32% result.

EXAMPLE 2

25 kg of thymus in the frozen state (starting temperature −30° C.) are precomminuted in a crushing mill and ground in a mincer (a total of 15 minutes) and are then homogenized with 75 liters of 0.9% strength sodium chloride solution, prepared from 74.3 kg of pyrogen free water, 675 g of sodium chloride and 0.75 g of phenylmethylsulfonyl chloride, at 0°–4° C. for 5 minutes in a 100 liter spray kettle. 3 rotor fillings of solid (15 kg moist weight) are separated off via a tube centrifuge (Cepa®), cooled to 0°–4° C., at 15,000×g, in the course of 1 hour, and are discarded. 83.6 kg of supernatant liquor are filtered over gauze, the filtrate is warmed to an internal temperature of +80° C. in a 100 liter spray kettle in the course of 20–25 minutes, while stirring, and the resulting precipitate (3 kg moist weight) is separated off in the course of 15 minutes by means of a cooled tube centrifuge at 15,000×g. The slightly opalescent supernatant liquor is filtered over 4 layers of gauze and is introduced into 375 liters of acetone, pre-cooled to −20° C., while stirring. After 2 minutes, the resulting precipitate is centrifuged off via a cooled tube centrifuge (15,000×g, 15 minutes). The centrifuge residue (500 g moist weight) is washed with 3 liters of acetone of −20° C., centrifuged off in a beaker centrifuge at 3,000×g in the course of 10 minutes and dried in a vacuum desiccator. 325 g of a slightly yellowish powder with a protein content of 25% result.

EXAMPLE 3

250 g of acetone powder according to Example 1 or 2 are dissolved in 2.5 liters of water and the solution is brought to pH 8.0 with 5N ammonium hydroxide and stirred at 0°−+4° C. for one hour. The insoluble content (about 50 g after drying) is centrifuged off with a beaker centrifuge at 5,000 rpm in the course of 30 minutes. After determination of the amount of protein by the conventionally used Lowry method, the supernatant liquor is adjusted to a protein content of about 25 mg/ml by adding 0.7 liter of water, 1 liter of saturated ammonium sulphate solution is added and the mixture is stirred at +4° C. for 1 hour. A precipitate forms and is separated off by centrifugation (5,000 rpm, 30 minutes). 628 g of ammonium sulfate are added to the clear supernatant liquor and the pH is brought to 4.0 with glacial acetic acid. After the mixture has been stirred at 0°−+4° C. for 1 hour, the resulting suspension is again subjected to centrifugation. The precipitate thereby obtained contains about 35 g of protein, determined by the Lowry method, in addition to a substantial amount of ammonium sulfate, and is therefore not dried, but used directly for the ultrafiltration.

EXAMPLE 4

The ammonium sulfate precipitate obtained from 250 g of acetone powder as described in Example 3 is dissolved in 1.5 liters of 0.1N ammonium bicarbonate (pH 8.0) to give a clear solution, and is subjected to ultrafiltration in an Amicon hollow fiber apparatus with 2 filter cartridges of the type H 10×50 (exclusion limit of 50,000 Daltons). The solution is thereby concentrated down to 300 ml, being replenished with two 500 ml portions of 0.1N ammonium bicarbonate (pH 8.0) towards the end of the ultrafiltration in order to achieve complete removal of all the proteins below 50,000 Daltons. 19.8 g of residue containing all the higher-molecular proteins is obtained after freeze-drying, the residue having a protein content, measured by the Lowry method, of 84%.

The filtrate is subjected to renewed ultrafiltration, this time in a 2.5 liter Amicon cell with a 5PM10 flat membrane (exclusion limit of 10,000 Daltons). The solution is thereby concentrated to 150 ml, being replenished with two 400 ml portions of 0.1N ammonium bicarbonate (pH 8.0) towards the end. Freeze-drying of the residue gives 8.2 g with a protein content of 89%.

A column 21.5 cm in diameter and 100 cm in length, filled with Sephadex G10 (coarse) and equilibrated with 0.1M ammonium bicarbonate (pH 8.0) is used to free the filtrate from salts, in particular ammonium sulfate. It is operated at a flow rate of 5 liters per hour. After about one third of the column volume, salt-free protein appears in the eluate, followed by a mixed fraction of protein and salt (protein content, measured by the Lowry method, 48%), which is subjected to rechromatography over the same column. 5.9 g of a material with a protein content of 93% are obtained in this manner, after freeze-drying.

EXAMPLE 5

17 g of a protein fraction obtained by ultrafiltration according to Example 4 are stirred with 500 ml of 0.1M sodium acetate buffer (pH 5.5). An insoluble residue (1.15 g after drying) is separated off by centrifugation (20 minutes, 5,000 rpm). 3 liters of CM-cellulose (Servacel CM-23), equilibrated with the same buffer, are added to the soluble content. After the mixture has been stirred for half an hour, the suspension is passed through a glass suction filter and the cation exchanger is filtered off with suction, until almost dry, and rinsed slowly with 2 liters of the same buffer.

The filtrate (2.5 liters) is freeze-dried and dissolved in 150 ml of 0.1M ammonium bicarbonate (pH 8.0), and the solution is demineralized, at a flow rate of 150 ml per hour, over a column 5 cm in diameter and 40 cm in length, filled with Sephadex G10 (coarse) and equilibrated with 0.1M ammonium bicarbonate (pH 8.0). In this case also, a fraction containing salt-free protein is initially obtained, followed by a mixed fraction of protein and salt, which is rechromatographed again over the same column. 9.1 g of a material with a protein content of 94%, called the fraction in the following text, are thus obtained, after freeze-drying.

EXAMPLE 6

30 g of a protein fraction obtained by ultrafiltration according to a Example 4 are stirred into 1 liter of 0.01M sodium acetate (pH 5.5), and an insoluble content (1.3 g after drying) is separated off by centrifugation (20 minutes, 5,000 rpm).

Figure 1:
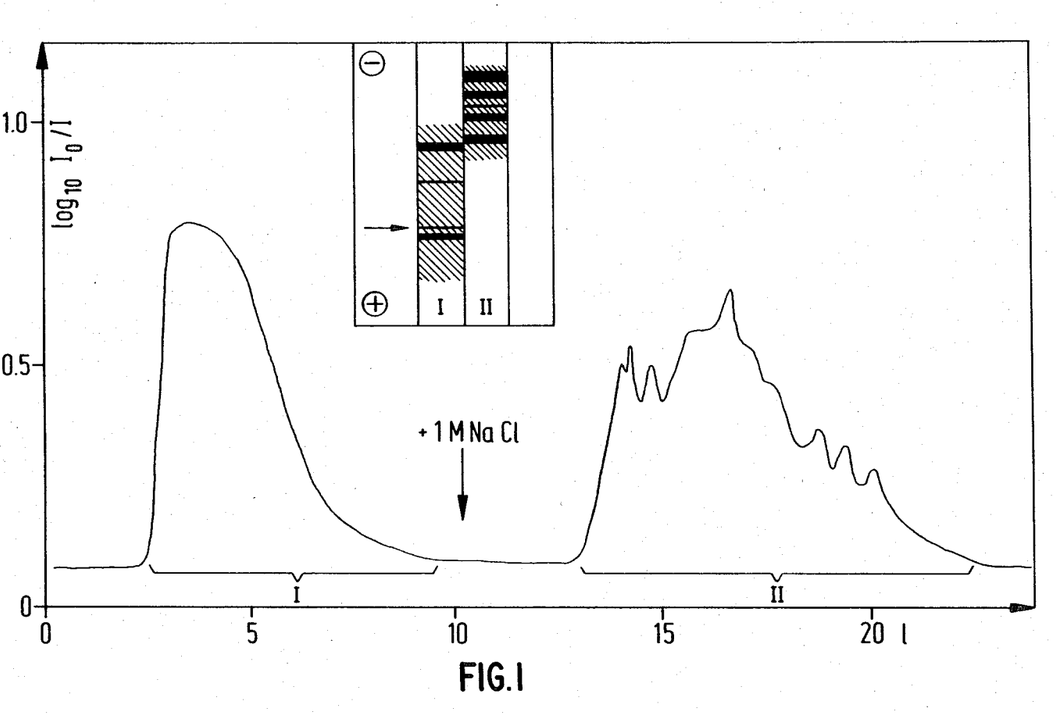

The clear solution is subjected to chromatography over a column 10 cm in diameter and 43 cm in length, filled with CM-cellulose (Servacel CM-32) and calibrated with 10 liters of 0.01M sodium acetate (pH 5.5), the column first being eluted with 10 liters of the same buffer at a flow rate of 500 ml per hour, after the sample has been applied. A peak (cf. FIG. 1) is thereby obtained, and is freed from salt components as described in Example 5. 17.5 g of a fraction (in the following designated as "CM1") with a protein content of 95% result from freeze-drying.

The column is washed free for renewed use by changing the buffer to 0.01M sodium acetate and 1.0M sodium chloride (pH 5.5). A further peak (cf. FIG. 1) is thereby obtained and, after demineralization in the conventional manner and freeze-drying, gives 11.5 g of protein.

EXAMPLE 7

A column 10 cm in diameter and 62 cm in length is filled with DEAE-Sephacel (Pharmacia), which has been preswollen in a buffer of 0.05M tris/HCl (trishydroxymethyl-aminomethane), and is equilibrated with 15 liters of the same buffer at a flow rate of 325 ml per hour.

17.5 g of CM1 are dissolved in 1 liter of 0.05M tris/HCl (pH 8.5) and the solution is pumped onto the column at 325 ml per hour. At the same rate, the column is rinsed with 1 liter of the same buffer and, finally, a linear gradient of 0 to 1.0M sodium chloride is applied over a volume of 36 liters. A large number of small peaks, which overlap to give a large main peak, become visible by detection at 245 nm (cf. FIG. 2). Each of these peaks is demineralized in the conventional manner and analyzed by basic polyacrylamide gel electrophoresis (PAGE). From this analysis, the substance sought is found, with an Rf value of 0.5–0.6, in the third peak of the main peak (labelled 2 in FIG. 2), containing 1.158 mg of protein.

Comparison of the PAGE of the peak containing the substance with that of the fraction eluted beforehand (cf. insert in FIG. 1) shows the scarcely avoidable overlapping of the individual peaks in this stage of the purification, making subsequent purification of the individual peaks also unavoidable.

EXAMPLE 8

A column 2.6 cm in diameter and 25 cm in length is filled with hydroxyapatite (Bio Rad) suspended in 0.01M sodium phosphate buffer (pH 6.8) and is equilibrated with 500 ml of the same buffer at a flow rate of 80 ml per hour.

400 mg of the fraction, containing the substance sought, from the anion exchange chromatography are dissolved in 50 ml of 0.01M sodium phosphate buffer (pH 6.8) and a linear gradient of 0.01–0.40M sodium phosphate (pH 6.8) is applied over 1.3 liters, with 80 ml of the same buffer (cf. FIG. 3). The substance sought is in the breakthrough peak (peak 1 in FIG. 3) and is isolated from this, in a yield of 290 mg, together with some other polypeptides, by dimineralization and freeze-drying carried out in the conventional manner.

The resulting material shows a similar band spectrum to the starting mixture in the PAGE, but with a considerably higher intensity of the band corresponding to the polypeptide according to the invention.

EXAMPLE 9

A column 1.6 cm in diameter and 120 cm in length is filled with Ultrogel ACA 54 (LKB), preswollen in 0.1M ammonium bicarbonate buffer (pH 8.0), and is equilibrated with 750 ml of the same buffer at a flow rate of 30 ml per hour.

Figure 4:
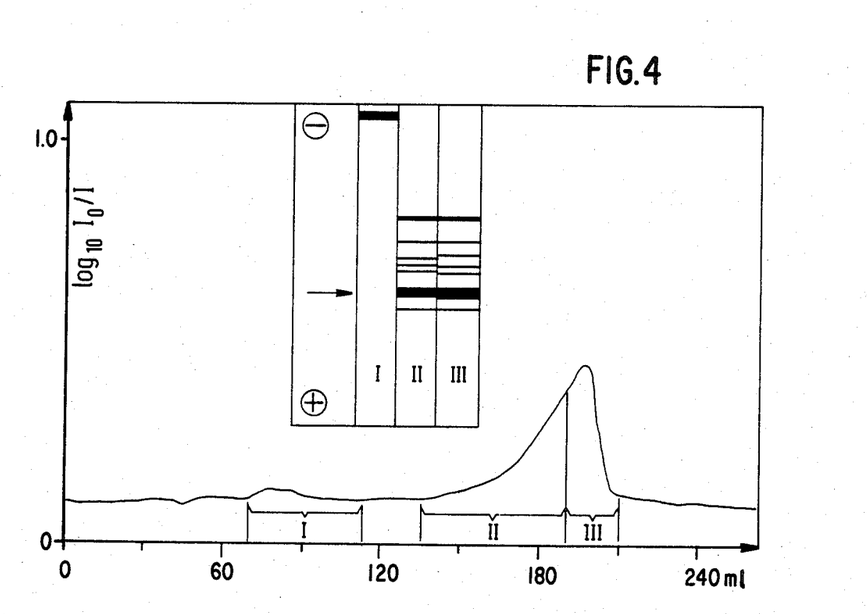

290 mg of the fraction, containing the substance sought, from the anion exchange chromatography are dissolved in 30 ml ammonium bicarbonate buffer (pH 8.0) and the solution is pumped onto the column at 30 ml per hour, the column then being further rinsed with the same buffer at the same flow rate (cf. FIG. 4).

A small breakthrough peak containing small amounts of high-molecular proteins, and, after twice the volume, a broad main peak which gives the same band spectrum in the PAGE throughout the entire volume, appear.

Freeze-drying of this main peak gives 200 mg of a material of only slightly better quality than the starting material.

EXAMPLE 10

A column 2.5 cm in diameter and 35 cm in length is filled with DEAE-Sephacel (Parmacia), preswollen in 0.005M tris/HCl (pH 0.8), is equilibrated with 500 ml of the same buffer at a flow rate of 60 ml per hour.

220 mg of the hydroxylapatite fraction containing the same substance is dissolved in 50 ml 0.05M tris/HCl (pH 8.0) and is pumped onto this column at a flow rate of 60 ml per hour. The column is then eluted, at the same rate, with a linear gradient of 0 to 0.3M sodium chloride over a volume of 2 liters (cf. FIG. 5).

A main peak composed of several peaks appears approximately in the middle of the gradient. If this is separated into 5 fractions (cf. FIG. 5), the substance according to the invention is predominantly in fraction 4. It can be isolated from this fraction in a yield of 70 mg and with a purity of over 90%, according to the PAGE, by demineralization and freeze-drying carried out in the conventional manner.

EXAMPLE 11: TYPICAL CLEAVAGE

An enzyme-substrate ratio of 1/100 at a concentration of 1 mg/ml of substrate in 0.1M N-methylmorpholine acetate buffer, pH 8.1, is used in the enzymatic cleavage. Incubation at 37° C. was carried out with TPCK-treated trypsin for 2 hours or with TLCK-treated α-chymotrypsin for 7 hours. After acidification to pH 2.5 with 6N glacial acetic acid, the solution was heated rapidly to 80° C. After 2 minutes, the solution was cooled again rapidly and centrifuged. The supernatant liquor was then lyophilized, whereupon a salt-free, white powder was obtained.

EXAMPLE 12: E-ROSETTE TEST

In the test, which is carried out by the method of Aiuti (Scand. J. Immunol., 3, 521–532, 1974), the rosette counts of Lymphocyte/erythrocyte systems are determined after incubation (37° C.) for 2 hours in the medium or in the medium+substance. In the assessment, of 200 cells counted, only those which consist of at least one lymphocyte and three erythrocytes are evaluated as rosettes.

The ratio of the number of rosettes after preincubation with substances and without substance, the stimulation Index $S_I$, is then a measure of the differentiation of the null cells to mature T cells induced by the substance.

| | Results: | |
|---|---|---|
| Dose μg/ml | Thymosin fraction V | Polypeptide according to the invention |
| 20 | $S_I = 1.9$ | $S_I = 3.1$ |
| 10 | 2.6 | / |
| 5 | 2.0 | 2.5 |
| 2.5 | 1.9 | / |
| 1.25 | 1.3 | 2.7 |

Whilst fraction V, as a mixture of various peptides of different biological activity, causes an increase in the rosette count from 17% to only 22% at a concentration of 1.25 μg/ml, incubation of the lymphocytes with 1.25 μg/ml of the peptide according to the invention leads to an increase in the rosette count from 18.5% to 50.5%.

EXAMPLE 12a: Phytohemaglutinin stimulation test

The substance(s) are introduced into the cell suspension in various concentrations ($10^5$ cells in 100 μl of RPMI 1640/Click+Hepes 20 mM, penicillin; streptomycin glutamine and 10% AB-serum inactivated by heat) about 1 μCi/well of tritium-labelled thymidine is added either after 48 hours or after 72 hours, the mixture is incubated for 8 hours, the cells are filtered off with suction on glass fibre filters and washed and the filters are later introduced into scintillation liquid and counted in a β-counter.

Since the substance(s) is present throughout the entire duration of the culture, possible degradation or change by serum or lymphocyte proteases cannot be excluded.

Results:

| Substance | Concentration PHA (μg/ml) | Incubation time (hours) | Dose (μg) | cpm | $\bar{x}_1$ | Control | $\bar{x}_2$ | $S = \frac{\bar{x}_1}{\bar{x}_2}$ |
|---|---|---|---|---|---|---|---|---|
| Polypeptide according to the invention | 10 | 48 | 1 | 24,772<br>20,334<br>17,791 | 20,965 | 16,216<br>12,730 | 14,472 | 1.45 |
| Mixture of fragments after tryptic cleavage | 10 | 48<br>43<br>72 | 1<br>2.5<br>2.5 | 19,257<br>22,817<br>20,967<br>7,994<br>9,116<br>8,705<br>14,606<br>15,598 | 21,013<br>8,621<br>15,522 | 7,468<br>6,815<br>8,910<br>12,177<br>13,710 | 7,731<br>12,943 | 1.45<br>1.12<br>1.24 |
| Mixture of fragments after chymotryptic cleavage | 20 | 72 | 1 | 37,624<br>42,771<br>41,972 | 40,456 | 25,247<br>37,921<br>34,058 | 32,409 | 1.25 |

EXPLANATION OF THE FIGURES

FIG. 1

The material obtained by ultrafiltration is fractionated on CM-Cellulose

10×43 cm Servacel CM 32 in 0.1M sodium acetate, pH 5.5
Flow rate: 500 ml per hour
Quantity introduced onto: 30 g
After 10 l: exchange of the buffer (now 0.1M sodium acetate, 1M sodium chloride, pH 5.5)

The insertion shows a picture of a basic electrophoresis on polyacrylamide gel.
yields:
fraction I: 17.5 g
fraction II: 11.5 g

FIG. 2

Fraction I obtained above is fractionated on DEAE-Cellulose

10×62 cm DEAE-Sephacel in 0.05M Tris/HCl, pH 8.5.
Flow rate: 350 ml per hour
Gradient of 0 to 1M sodium chloride over a volume of 36 l
Quantity introduced onto: 17.5 g The insertion shows a picture of a basic eletrophoresis on polyacrylamide gel.
yields:
fraction I: 722 mg
fraction II: 1.158 mg

FIG. 3

A fraction obtained from DEAE-Cellulose is purified on hydroxylapatite 2.6×25 cm hydroxylapatite in 0.01M sodium phosphate, pH 6.8
Flow rate: 80 ml per hour
Gradient of 0.01 to 0.40M phosphate (pH 6.8) over a volume of 1.3 l
Quantity introduced onto: 400 mg The insertion shows a picture of a basic electrophoresis on polyacrylamide gel.
yields:
fraction I: 290 mg
fraction II: 40 mg
fraction III: 9 mg

FIG. 4

Gel permetation chromatography of a fraction obtained from DEAE-Cellulose 1.6×120 cm Ultragel ACA 54 in 0.1M ammonium hydrogencarbonate, pH 8.0
Flow rate: 30 ml per hour
Quantity introduceed onto: 290 mg The insertion shows a picture of a basic electrophoresis on polyacrylamide gel.
yields:
fraction I: 2 mg
fraction II: 72 mg
fraction III: 128 mg

FIG. 5

Re-chromatography of fraction I, obtained from hydroxylapatite, on DEAE-Cellulose 2.5×35 cm DEAE-Sephacel in 0.05M Tris/HCl, pH 8.0
Flow rate: 60 ml per hour
Gradient of 0 to 0.3M sodium chloride over a volume of 2 l.

Quantity introduced onto: 220 mg

The insertion shows a picture of a basic electrophoresis on polyacylamide gel.
yields:
fraction I: 28 mg
fraction II: 53 mg
fraction III: 42 mg
fraction IV: 70 mg
fraction V: 12 mg

We claim:

1. A peptide cleavage product of a polypeptide having an action on the immunological system or of the pharmacologically acceptable salts of said polypeptide, said polypeptide having a molecular weight of 3,480, a UV absorption with a maximum at 205 to 210 nm, an isoelectric point at 3.95±0.15 and the following aminoacid composition: 4 asparaginic acid units, 3 threonine units, 3 serine units, 6 glutamic acid units, 1 glycine unit, 4 alanine units, 3 valine units, 1 isoleucine unit, 1 leucine unit, 5 lysine units and 1 arginine unit, and N-terminal, if appropriate, carrying an acyl group having 1 to 6 carbon atoms or an acylglycyl group, the acyl group of which has 1 to 6 carbon atoms, and said peptide cleavage products comprising 4 or more amino acids.

2. A pharmaceutical composition comprising an effective amount of the peptide cleavage product as claimed in claim 1 and a pharmaceutically acceptable carrier.

3. A method of treating virus infections, immunodeficiency diseases, oncogenesis, or accelerated aging processes comprising administering an effective amount of the peptide cleavage product as claimed in claim 1.

* * * * *